United States Patent [19]
Yada

[11] Patent Number: 5,200,706
[45] Date of Patent: Apr. 6, 1993

[54] APPARATUS FOR MEASURING IONIC CONCENTRATION IN TWO MEASUREMENT CONFIGURATIONS

[75] Inventor: Takaaki Yada, Kyoto, Japan

[73] Assignee: Horiba, Ltd., Kyoto, Japan

[21] Appl. No.: 681,729

[22] Filed: Apr. 8, 1991

[30] Foreign Application Priority Data

Apr. 9, 1990 [JP] Japan .................................. 2-38370

[51] Int. Cl.[5] .............................................. G01N 27/06
[52] U.S. Cl. ..................................... 324/446; 324/441;
324/450; 422/82.03
[58] Field of Search ............... 324/438, 439, 441, 446,
324/450; 422/82.03, 82.02

[56] References Cited

U.S. PATENT DOCUMENTS

| | | | |
|---|---|---|---|
| 4,123,701 | 10/1978 | Josefsen et al. | 324/724 X |
| 4,473,458 | 9/1984 | Schwartz et al. | 324/438 X |
| 4,608,532 | 8/1986 | Ibar et al. | 324/438 X |
| 4,918,391 | 4/1990 | Byrd | 324/446 |
| 4,940,946 | 7/1990 | Nazaryan | 324/438 |
| 5,096,669 | 3/1992 | Lauks et al. | 324/438 X |

Primary Examiner—Jack B. Harvey
Assistant Examiner—Glenn W. Brown
Attorney, Agent, or Firm—Price, Gess & Ubell

[57] ABSTRACT

A device for measuring ionic concentration in a sample liquid, having a detachable waterproof electrode housing. A body member has a computing device disposed therein and a display panel on an exterior surface. The waterproof electrode housing is demountably coupled to the body member. The electrode housing includes a flat surface sensor capable of measuring ionic concentration of the sample liquid when the device is placed on a flat surface, and is waterproof for measuring ionic concentration by immersion. A gap is formed between the body and the flat surface for preventing water from entering the body when the flat surface ionic concentration measurement procedure is being conducted.

15 Claims, 4 Drawing Sheets

APPARATUS FOR MEASURING IONIC CONCENTRATION IN TWO MEASUREMENT CONFIGURATIONS

FIELD OF THE INVENTION

The present invention relates to devices used for measuring pH or ionic concentration and, more specifically, to an apparatus for measuring ionic concentration.

BACKGROUND OF THE INVENTION

A prior art ionic concentration measuring apparatus 65 is shown in FIG. 6A. The measuring apparatus has a body 62 with an operating display 61 on an exterior surface 80. A cylindrical member 64 is made integral at an end 82 of the body 62, and includes a measuring electrode 63.

FIG. 6B shows a prior art pocket-sized, substantially flat measuring device 69. The flat measuring device 69 includes a flat body 67 constructed similar to a card-type pocket calculator. The flat body 67 has an operating display 66 on a flat exterior surface 84. A flat surface sensor 68 is located on the body's surface 84.

Both prior art devices 65, 69 are manufactured by Horiba, Ltd., Japan, and are disclosed in pending Japanese Patent Application No. Sho 61-285371 and Japanese Patent Application Laid-Open No. Sho 63-138255.

A disadvantage of the immersion measuring apparatus 65 is that it is necessary for the cylindrical member 64 and the measuring electrode 63 to be immersed in the liquid to be tested 70. If there is not sufficient liquid to be tested 70 in order to fully immerse the measuring electrode 63, then the liquid 70 cannot be measured.

The flat measuring device 69 allows ionic concentrations to be measured by merely dropping a small quantity of liquid to be tested 70 onto the flat surface sensor 68 by a syringe 71. However, the flat device 69 must be placed on a substantially flat surface for the device 69 to operate properly. Further, the structure of the body 67 is not waterproof, and if the liquid to be tested 70 or other moisture is spilled on or around the body 67, water may enter the body 67, substantially affecting measurements being conducted.

OBJECTS OF THE INVENTION

It is therefore an object of the present invention to provide an improved apparatus for measuring ionic concentration;

It is another object of the present invention to provide an apparatus capable of measuring ionic concentrations on a flat surface;

It is yet another object of the present invention to provide an apparatus capable of measuring ionic concentrations using immersion techniques; and It is yet still another object of the present invention to provide an apparatus for measuring ionic concentrations having a substantially waterproof body.

SUMMARY OF THE INVENTION

These and other objects and advantages of the present invention are achieved by providing an apparatus for measuring ionic concentrations having a body member and a waterproof electrode housing which allows both flat surface testing and immersion testing. In the preferred embodiment, the electrode housing includes a flat surface sensor for conducting flat surface measurements and is itself waterproof to allow immersion testing. The body member may also include a computing means, coupled to an operating display located on an exterior surface of the body member.

During flat surface measurements the apparatus of the preferred embodiment is placed on a flat surface in order to maintain the flat surface sensor in a substantially horizontal position. A platform, made integral with a bottom surface of the electrode housing, and a clip, made integral with a bottom surface of the body, maintain the body above the flat surface and form a small space between the body and the flat surface. This space prevents water from entering the body and damaging the computing means.

The flat surface sensor may also be immersed into liquid for conducting a desired immersion measurement. The electrode housing provided around the flat surface sensor is a waterproof structure, so that water may not enter the electrode housing.

BRIEF DESCRIPTION OF THE DRAWINGS

The present invention, both as to its organization and manner of operation, together with further objects and advantages, may be understood by reference to the following drawings.

DESCRIPTION OF THE PREFERRED EMBODIMENT

The following description is provided to enable any person skilled in the art to make and use the invention and sets forth the best modes contemplated by the inventor of carrying out his invention. Various modifications, however, will remain readily apparent to those skilled in these arts, since the generic principles of the present invention have been specifically defined herein.

Figure 1:
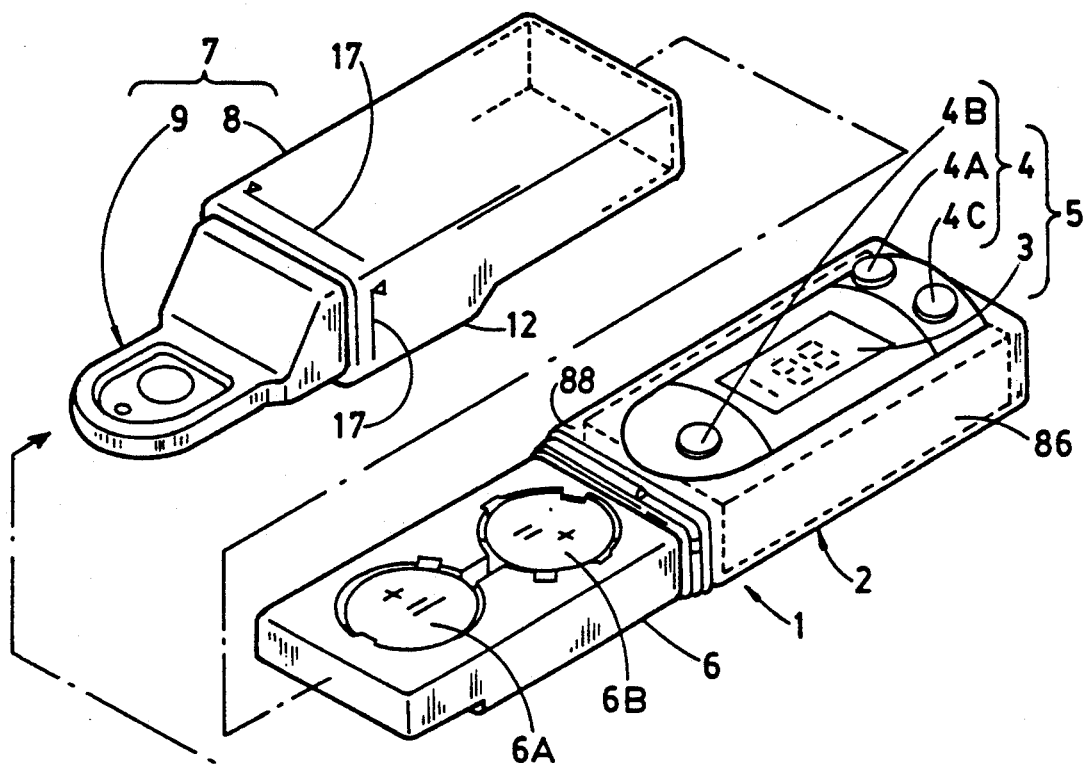
FIG. 1 is an exploded perspective view of the preferred embodiment of the present invention.
Figure 2:
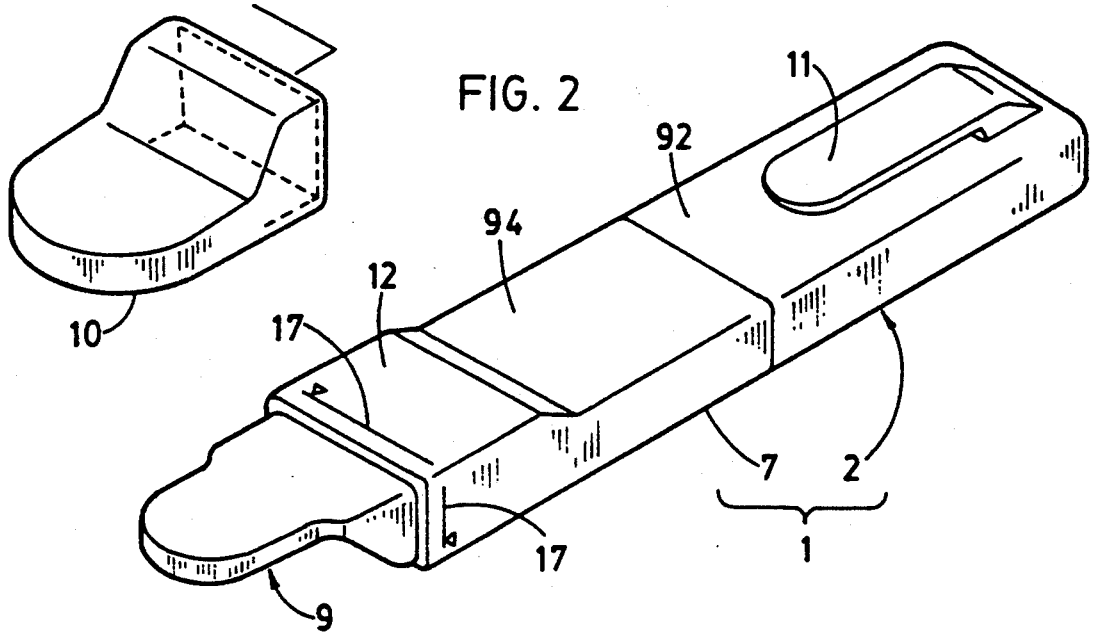
FIG. 2 is a perspective view of the preferred embodiment of FIG. 1.
Figure 3:
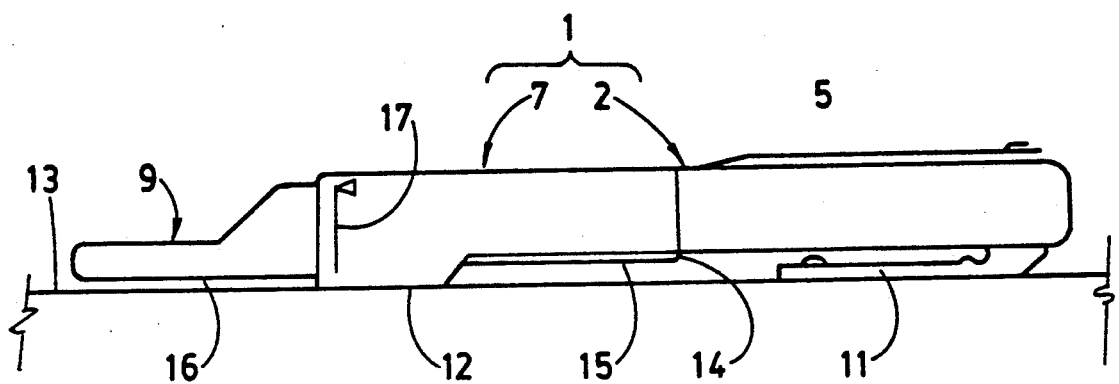
FIG. 3 is a plan view showing the preferred embodiment placed on a substantially flat surface.

Referring to FIGS. 1 through 3, there is shown a preferred embodiment of an ionic concentration measuring apparatus 1 constructed according to the principles of the present invention. A body member 2 may be made of plastic and has a computing means 86, such as a microcomputer. A display panel 5 is located on a top surface 88 of the body member 2 and is coupled to the computing means 86.

The display panel 5 includes a display screen 3 for reading computer data and a plurality of input buttons 4 for operating the computing means 86. The input buttons 4 include a power button 4A, a calibration button 4B, and a holding button 4C. Made integral with the body 2 is a power supply 6 that includes a pair of circular button cells 6A, 6B. The cells 6A, 6B are disposed on the apparatus' top side 88. In the preferred embodiment, the body member 2 does not need to be substantially waterproof.

An electrode housing 7 is adapted to slide over the power supply 6 and detachably couple to the body member 2. The electrode housing 7 may be fabricated using suitable plastics, and is assembled to be substantially waterproof. The electrode housing 7 includes an elongated hollow, rectangular encasing member 8 for encasing the power supply 6 and a substantially flat surface sensor housing 9 coupled to the encasing member 8. A protective plastic cap 10 is detachably mounted to the sensor housing 9 for protection. The total length of the preferred embodiment of the invented apparatus 1 is slightly greater than 10 centimeters and may be retained in a clothes pocket.

On a back surface 92 of the body member 2 is a clip 11. The clip 11 may hold the apparatus 1 in the pocket of a shirt. A back surface 94 of the encasing member 8 includes an elongated platform 12 that extends toward the sensor housing 9.

With reference to FIG. 3, the platform 12, in combination with the clip 11, maintains the body member 2 above a desired surface 13 so that a small space 15 is formed between the body member 2 and the flat surface 13. The small space 15 prevents water or other liquids from entering the body member 2 and damaging the computing means 86.

In the preferred embodiment, the platform 12 extends to the surface sensor housing 9 and provides a small gap 16 between the sensor housing 9 and the flat surface 13. A level line 17 located on the encasing member 8 is for indicating the maximum length that the electrode housing 7 should be immersed in a liquid to be tested.

Figure 4:
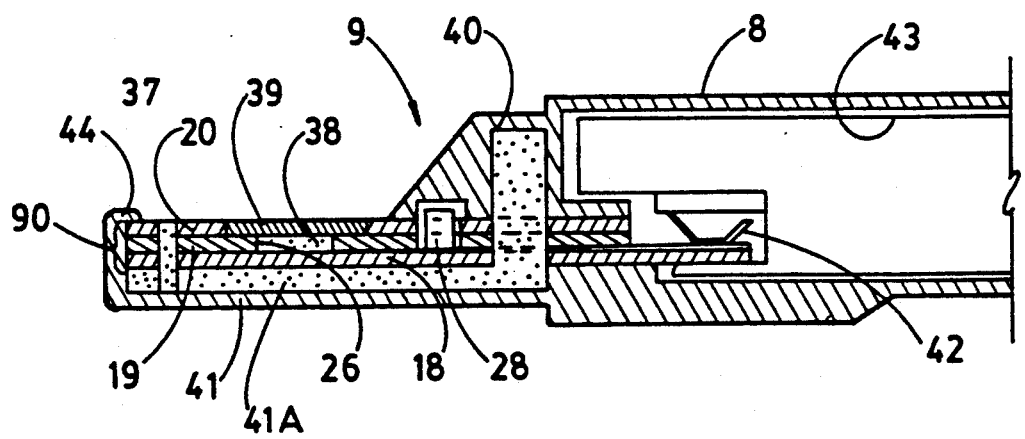
FIG. 4 is a cross-sectional view showing an electrode housing used in the preferred embodiment.
Figure 5:
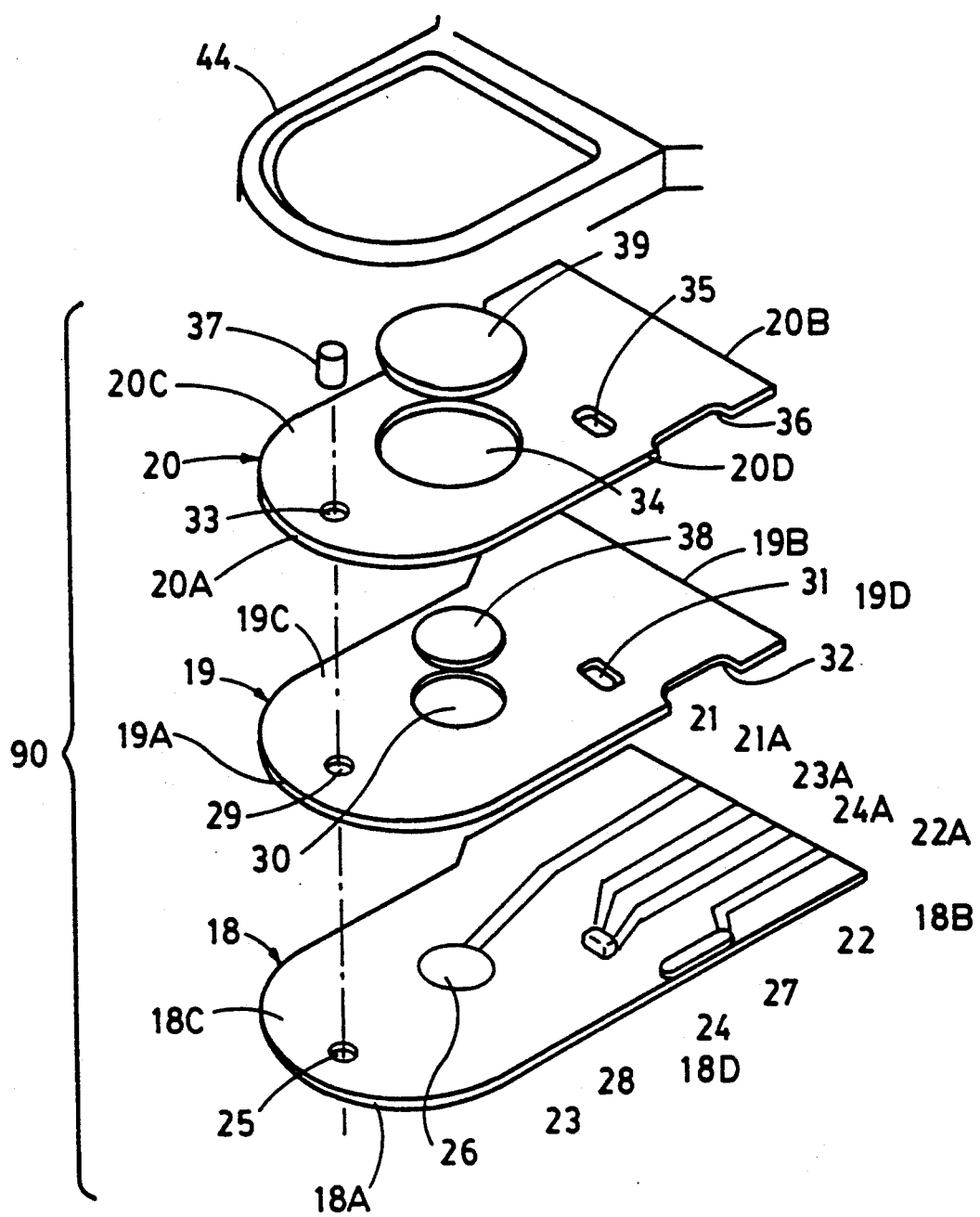
FIG. 5 is an exploded perspective view showing a flat surface sensor used in the preferred embodiment.
Figure 6A:
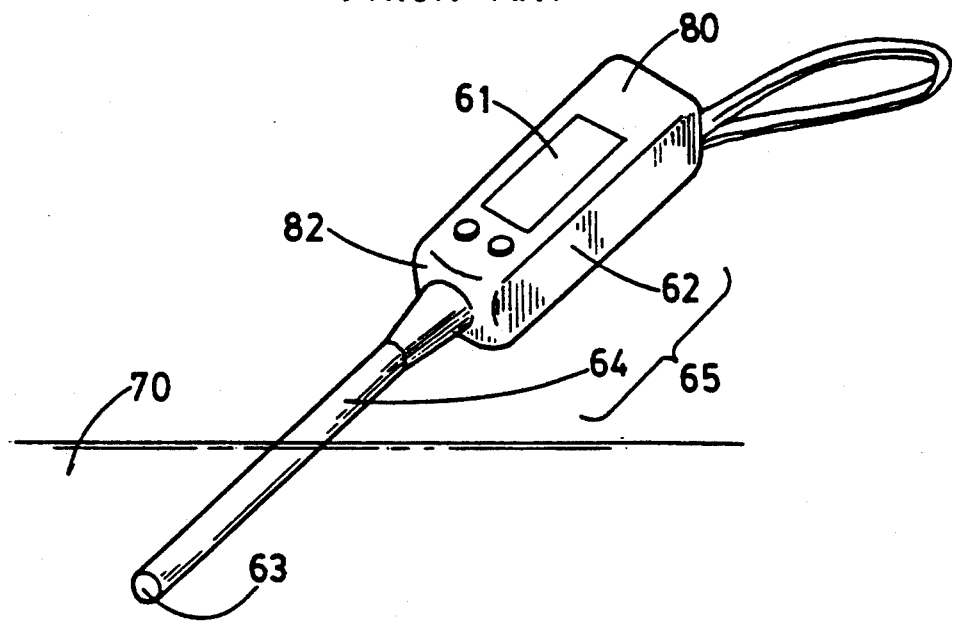
FIGS. 6A and 6B are perspective views of prior art measuring apparatus.
Figure 6B:
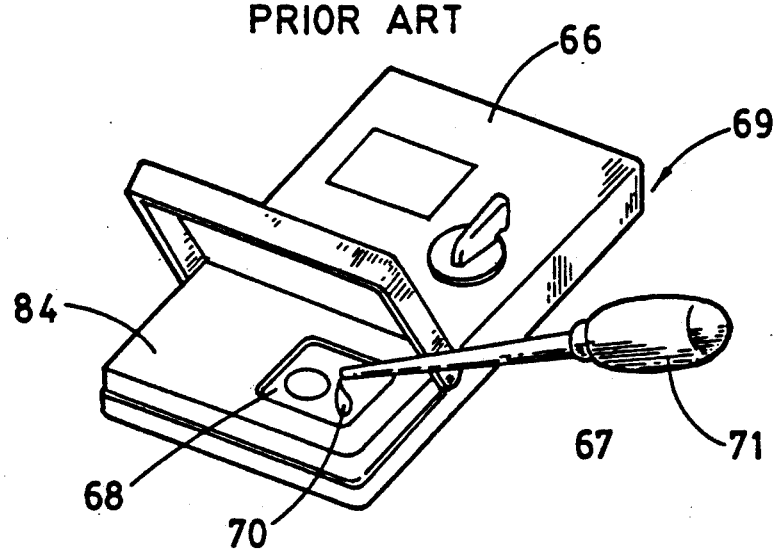

With reference to FIGS. 4 and 5, the construction of the electrode housing 7 will be more fully discussed. The sensing electrode 90 includes three substrates 18, 19, 20 of a material that is highly insulative, even when immersed in a solution containing an electrolyte. The substrates 18, 19, 20 may be made of suitable insulative materials such as polyethylene terephthalate (PET). Each substrate 18, 19, 20 includes an arched end 18A, 19A, 20A and a straight end 18B, 19B, 20B. The overall length of the first substrate 18 is slightly greater than the lengths of the second and third substrates 19, 20.

The first substrate 18 is provided with a plurality of electrically-conductive strips 21, 22, 23, 24 formed on its upper surface 18C. The conductive strips 21, 22, 23, 24 may be placed on the first substrate's upper surface 18C by pretreating the upper surface 18C, then printing an Ag paste using a silk screening process.

A substantially small circular hole 25 is disposed through the first substrate 18. The outside conductive strip 21 has a substantially circular end portion 26 located approximately at the center of the first substrate 18. The circular end 26 is coated with AgCl to form a glass electrode.

The other outside conductive strip 22 has an elongated end 27 located along a side 18D of the first substrate 18. The conductive strip's elongated end 27 may be coated with AgCl to form an inner reference electrode.

A temperature-compensating element 28, such as a thermistor, is affixed to the ends of the center conductive strips 23, 24 distal to the first substrate's straight side 18B. Each conductive strip 21, 22, 23, 24 includes a lead 21A, 22A, 23A, 24A which is located flush with the first substrate's straight end 18B.

The second substrate 19 includes a substantially small, circular opening 29 aligned with the small circular opening 25 in the first substrate 18. A substantially large circular opening 30 is disposed through the second substrate 19 in substantial alignment with the glass electrode 26 located on the first substrate's upper surface 18C. The large opening 30 has a diameter slightly greater than that of the glass electrode 26.

A substantially small, rectangular opening 31, in substantial alignment with the thermistor 28, is disposed through the second substrate 19. The rectangular opening 31 is similar to the thermistor in length and width. An elongated notch 32 is formed in a side 19B of the second substrate 19 for accommodating the elongated reference electrode 27.

The third substrate 20 has a substantially small opening 33 disposed therethrough in substantial alignment with the previous small openings 29, 25 in the first and second substrates 18, 19. The third substrate's small opening 33 has the same diameter as the previous small openings 25, 29. A substantially large circular opening 34 is disposed through the third substrate 20 in substantial alignment with the second substrate's large circular opening 30 and the first substrate's glass electrode 26. The large circular opening 34 has a diameter slightly larger than that of the circular opening 30 in the second substrate 19.

A rectangular opening 35 is disposed through the third substrate 20 in substantial alignment with the second substrate's rectangular opening 31. The third substrate's rectangular opening 35 is substantially the same length and width as the other rectangular opening 31. An elongated notch 36 is disposed through a side 20D in the third substrate 20 corresponding to the second substrate's notch 32. The third substrate's notch 36 and second substrate's notch 32 afford access to the reference electrode 27.

An electrical liquid junction 37 is adapted to extend through the small openings 25, 29, 33. The electrical junction 37 comprises a gel-impregnated, hydrophilic, high molecular porous member made of a sintered molded body from an olefin family high polymer powders. One such powder is SUN FINE AQ made by Asahi Kasei KK, Japan. The high molecular porous junction 37 has a mechanical strength substantially similar to that of polyolfines and has a hydrophilicity which is achieved by a denaturing treatment. In the preferred embodiment, the junction 37 is impregnated with a so-called undrying out gel composite. The gel composite may comprise a water-saturated jelly compound containing an Na salt and an acrylic polymer. The gel composite is commercially available under the trade name U JELLY, manufactured by Showa Denko KK, Japan. The gelatine composite does not deposit KCl, and does not lose wetness on the surface of the junction 37.

A circular gelatinized internal liquid 38 is retained in the second substrate's large circular opening 30. The circular internal liquid 38 may be fabricated using a gelatinizing agent such as agar-agar, gelatin glue, or various other gelatinizing agents found in the acryl family of hygroscopic polymers. A gel evaporating agent, such as glycerine or ethylene glycol, is added to the gelatinizing agent to evaporate the liquid. The circular liquid 38 is obtained by adding a phosphoric acid buffer solution to a AgCl-super saturated 3.3 M-KCl solution formed into a disk-like shape. The circular liquid 38 is then placed into the opening 30 by first heating the liquid 38 to transform it into a paste, then placing it into the opening so that it extends slightly above an upper surface 19C of the second substrate 19.

A glass responsive membrane 39 used for measuring pH is disposed through the third substrate's large opening 34 and coupled to the liquid 38. The glass responsive membrane 39 is adhered to the liquid 38 using suitable adhesives, and is affixed so that its upper surface is substantially level with an upper surface 20C of the third substrate 20.

An L-shaped cavity 41 is located in the sensor housing 9 between the sensor housing 9 and the encasing member 8. The cavity 41 is filled with a gelatinized liquid 40, of a chemical composition similar to the circular internal liquid 38. An elongated portion 41A of the L-shaped case extends through the sensor housing 9, below the first substrate 18. A substantially short portion 44 of the cavity 41 extends above the third substrate 20 perpendicular to the sensing electrode 90. The gelatinized liquid 40 comes in contact with the reference electrode 27 through the notches 36, 32. The lower portion of the electrical junction 37 extends into the L-shaped cavity's elongated portion 41A and combines with the gelatinized liquid 40.

An electrical contact 42 is used to couple the computing means 86 to the conductive strip's leads 21A, 22A, 23A, 24A through a conductive wire 43.

In operation, the sensor housing 9 is held horizontal by placing the pH measuring apparatus 1 on a suitable flat surface 13. The flat surface measurement is conducted by sequentially dropping substantially small quantities of liquid to be tested (not shown) onto the flat surface sensor 90. The small space 15 formed by the platform 12 and clip 11 prevents Water from entering the body 2 when undergoing the flat surface measurement process.

When using the invented apparatus' preferred embodiment 1 for an immersion measurement, the sensor housing 9 is immersed into the liquid to be tested until the liquid reaches the level line 17. In an alternative embodiment, the electrode housing 7 may be made integral with the body member 2 and the entire apparatus 1 would be waterproof.

The preferred embodiment 1 is capable of measuring various kinds of ions, such as $Na^+$ and $K^+$, in addition to the measurement of pH. Other ion types may be measured using different electron housings capable of measuring such ions. The electrode sensor 90 includes a three-piece substrate having a printed circuit that embodies conductive strips 21, 22, 23, 24 on only one surface, so that the sensing electrode 90 and the sensor housing 9 can be easily mass produced. The temperature-compensating element 28, incorporated in the flat surface sensor 90, can compensate for the varying temperatures of liquid to be tested.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. An apparatus for measuring ionic concentration in a sample liquid comprising:
    a body; and
    measuring means attached to the body for measuring the ionic concentration of the sample liquid and producing a signal representative of the measured concentration, the measuring means including a sensor means having a substantially flat surface sensor including a plurality of laminated substrates and a printed circuit interposed between a center and a lowermost substrate, the measuring means operative in a first position by placing the sample on the measuring means when the body is on a substantially flat surface and operative in a second position by immersing the measuring means within the sample.

2. The apparatus of claim 1, wherein the measuring means is detachable from the body.

3. The apparatus of claim 2, wherein the measuring means is a waterproof electrode housing slidably detachable to the body.

4. The apparatus of claim 1 wherein the measuring means is a waterproof electrode detachably coupled to the body.

5. The apparatus of claim 4 wherein the flat sensor means measures the sample liquid when the apparatus is placed on a flat surface, the electrode being waterproof for immersion into a sample liquid.

6. The apparatus of claim 1, wherein the body includes a power supply, computing means, and a display panel to produce a representative display of the measured ionic concentration.

7. The apparatus of claim 6, wherein the body further includes control means for allowing operation, input, and memory.

8. The apparatus of claim 1, wherein an immersion line is marked on the apparatus to show the maximum level of immersion in the second operative position.

9. The apparatus of claim 1, wherein a lifting means is affixed to a bottom surface of the body to elevate the body above any liquid on the flat surface.

10. The apparatus of claim 9, wherein the lifting means is a clip adaptable to hold the apparatus in place.

11. The apparatus of claim 1, wherein a temperature compensating means is incorporated within the measuring means.

12. An apparatus for measuring ionic concentration in a sample liquid, comprising:
    a body including a computing means;
    a detachably mounted electrode housing mounted upon the body, the electrode housing being waterproof to prevent fluid from entering the housing or the body during measurement in several measurement configurations, the electrode housing including a flat sensor housing having a sensing electrode, the sensing electrode adapted to measure the ionic concentration of the sample liquid in the several measurement configurations including:
        a first measurement configuration when the flat sensor housing is immersed within the sample liquid; and
        a second measurement configuration when the body including the mounted electrode housing is placed upon a flat surface and the sample liquid is disbursed upon the sensing electrode; and
    a lifting means affixed to the body such that a small gap is formed between the body and the flat surface in the second configuration when the apparatus is undergoing a flat surface measurement, the small gap being sufficiently large to prevent fluid on the flat surface from entering the body and damaging the computing means.

13. An apparatus for measuring ionic concentration in a sample liquid, comprising:
    a body including a computing means;
    a detachably mounted electrode housing including a flat sensor housing having a sensing electrode, the sensing electrode adapted to measure the ionic concentration of the sample liquid when the flat sensor housing is immersed therein, and the sensing electrode adapted to measure the ionic concentration of the sample liquid disbursed thereon when the apparatus is placed on a flat surface; and a lifting means affixed to the body such that a small gap is formed between the body and the flat surface on which the body is placed when undergoing a flat surface measurement, the small gap being sufficiently large to prevent fluid on the flat surface from entering the body and damaging the computing means.

14. The apparatus for measuring ionic concentration of claim 13, wherein the sensing electrode comprises a plurality of laminated substrates having a printed circuit interposed between a center substrate and a lowermost substrate.

15. The apparatus for measuring ionic concentration of claim 14, wherein a temperature-compensating element is disposed in the printed circuit.

* * * * *